United States Patent [19]
Chen et al.

[11] Patent Number: 5,959,136
[45] Date of Patent: Sep. 28, 1999

[54] PROCESS FOR THE PREPARATION OF MALONONITRILE

[75] Inventors: Peter Chen; Johannes Hoffner, both of Zürich; AndréMueller, Geroldswill; Rudolf Fuchs, Sion, all of Switzerland

[73] Assignee: Lonza, Ltd., Gampel/Valais, Switzerland

[21] Appl. No.: 09/272,164

[22] Filed: Mar. 19, 1999

[30] Foreign Application Priority Data

Mar. 19, 1998 [CH] Switzerland .............................. 0665/98

[51] Int. Cl.$^6$ .................................................. C07C 255/00
[52] U.S. Cl. .............................................................. 558/453
[58] Field of Search ............................................... 558/453

[56] References Cited

PUBLICATIONS

Ullman's Encyklopä die der Technischen Chemie, 4$^{th}$ Revised and Expanded Edition, Verlag Chemie Weinheim, vol. 16, pp. 419–423.
Agnew. chemie, (1965), 77, 492–504.
J. Am. Chem. Soc., (1981), 013, 767–772.

*Primary Examiner*—Johann Richter
*Assistant Examiner*—Joseph Murray
*Attorney, Agent, or Firm*—Fisher, Christen & Sabol

[57] ABSTRACT

A novel process for the preparation of malononitrile, which involves subjecting an isonitrile, optionally in the presence of a nitrile, to a high-temperature treatment.

4 Claims, No Drawings

PROCESS FOR THE PREPARATION OF MALONONITRILE

BACKGROUND OF THE INVENTION

1. Field of the Invention

The invention relates to a novel process for the preparation of malononitrile or of derivatives of malononitrile of the general formula:

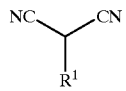

I in which $R^1$ is hydrogen, an alkyl group or a cycloalkyl group.

2. Background of the Invention

Malononitrile is a starting material and intermediate of central importance for the preparation of an extremely wide range of, for example, pharmaceutical or agrochemical active ingredients (Ullmann's Encyklopädie der technischen Chemie, 4$^{th}$ revised and expanded edition, Verlag Chemie Weinheim, Volume 16, pp. 419–423).

Although a large number of processes are known for the preparation of malononitrile, the only one to have achieved significance on an industrial scale is the high-temperature reaction of acetonitrile with cyanogen chloride at temperatures above 700° C.

BROAD DESCRIPTION OF THE INVENTION

The object of the invention is to develop an alternative process with the potential for use on an industrial scale. The object of the invention is achieved by the process of the invention.

According to the invention, an isonitrile of the general formula:

$R^2$—NC     II in which $R^2$ is an alkyl group or a cycloalkyl group, is converted, optionally in the presence of a nitrile of the general formula:

$R^3$—CN     III in which $R^3$ is hydrogen, an alkyl group or a cycloalkyl group, at a temperature of from 700° to 1000° C.

DETAILED DESCRIPTION OF THE INVENTION

An alkyl group is expediently taken to mean a $C_{1-6}$-alkyl group, namely, methyl, ethyl, n-propyl, isopropyl, n-butyl, isobutyl, t-butyl, pentyl and its isomers or hexyl and its isomers. A preferred alkyl group is methyl.

Cycloalkyl is expediently a $C_{3-6}$-cycloalkyl, namely, cyclopropyl, cyclobutyl, cyclopentyl or cyclohexyl. Preference is given to the conversion of methylisonitrile using acetonitrile.

Since the isonitriles of the general formula II can isomerize to the corresponding nitriles, it is possible, during their conversion using the nitriles of the general formula III, to obtain derivatives of malononitrile, the $R^1$ group of which can correspond either to the $R^2$ group of the isonitrile or to the $R^3$ group of the nitrile. This result is, of course, provided that $R^2$ and $R^3$ are different. Accordingly, such a conversion can produce any mixtures of the derivatives of malononitrile.

The isonitriles of the general formula II are either commercially available or can by synthesized by known processes in the literature, e.g., Agnew. Chemie, 1965, 77, 492–504 or J. Am. Chem. Soc., 1981, 103, 767–772.

The high-temperature conversion according to the invention preferably proceeds at a temperature of from 800° to 950° C.

The reaction is usually carried out in a tubular reactor, which is optionally provided with suitable packing.

The conversion time is generally a few seconds.

The malononitrile can be isolated from the reaction product, for example, by extraction using a suitable solvent.

EXAMPLE 1

Synthesis and purification of malononitrile by thermolysis of methyl isocyanide and acetonitrile 2 ml of methyl isocyanide was diluted with 3 ml of acetonitrile and, using a syringe, introduced into a vapor stream of an acetonitrile distillation (15 g over 20 minutes). The vapor stream was introduced into a quartz pyrolysis tube (length 30 cm, internal diameter 2.5 cm) heated to 870° C. The reaction product was collected in a cool trap cooled to –50° C. The cool trap residue was concentrated by evaporation on a rotary evaporator, and the content of the reaction products (516 mg) was determined by $^1$H NMR, namely:

| | |
|---|---|
| Malononitrile | 18 percent |
| Succinonitrile | 1 percent |
| Fumaronitrile and maleonitrile | 1 percent |

The crude product was extracted with chloroform. Only malononitrile and succinonitrile was soluble in this extract.

EXAMPLE 2

Synthesis of malononitrile by thermolysis of methyl isocyanide and acetonitrile 2 ml of methyl isocyanide was diluted with 3 ml of acetonitrile and, using a syringe, introduced into a vapor stream of an acetonitrile distillation (15 g over 20 minutes). The vapor stream was introduced into an equilibrated quartz pyrolysis tube (length 30 cm, internal diameter 2.5 cm) heated to 920° C. The reaction product was collected in a cool trap cooled to –50° C. The cool trap reside was concentrated by evaporation on a rotary evaporator, and the content of the reaction products (1400 mg) was determined by $^1$H NMR, namely:

| | |
|---|---|
| Malononitrile | 40 percent |
| Succinonitrile | 1.5 percent |
| Fumaronitrile and maleonitrile | 9 percent |

The following examples were carried out as in Example 2, but at different quartz tube temperatures.

| | Temperature in °C. | Acrylonitrile | Succinonitrile | Fumaronitrile and maleonitrile | Malononitrile |
|---|---|---|---|---|---|
| 3 (Comp.) | 670° | 0 | 0 | 0 | 0 |
| 4 (Inv.) | 770° | | 1 | 0.2 | 1.1 |
| 5 (Inv.) | 820° | | 0.6 | 0.4 | 4 |

-continued

| | Temperature in °C. | Acrylo-nitrile | Succino-nitrile | Fumaronitrile and maleonitrile | Malono-nitrile |
|---|---|---|---|---|---|
| 6 (Inv.) | 845° | | 0.8 | 1 | 12 |
| 7 (Inv.) | 870° | | 0.5 | 2.5 | 18 |
| 8 (Inv.) | 895° | 2 | 1 | 5 | 33 |
| 9 (Inv.) | 920° | 10 | 1.5 | 8 | 40 |
| 10 (Inv.) | 945° | 33 | 1 | 17 | 35 |
| 11 (Inv.) | 970° | 28 | 2 | 20 | 29 |
| 12 (Comp.) | 1070° | 0 | 0 | 0 | 0 |

Notes:
Comp. = Comparison
Inv. = Invention

What is claimed is:

1. A process for the preparation of malononitrile or a derivative of malononitrile of the formula:

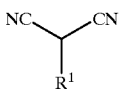
I in which $R^1$ is hydrogen, an alkyl group or a cycloalkyl group, characterized in that an isonitrile of the formula:

$R^2$—NC  II in which $R^2$ is an alkyl group or a cycloalkyl group, is converted, optionally in the presence of a nitrile of the formula:

$R^3$—CN  III in which $R^3$ is hydrogen, an alkyl group or a cycloalkyl group, at a temperature of from 700° to 1000° C.

2. The process according to claim 1, wherein the isonitrile of the formula II is methylisonitrile, and the nitrile of the formula III is acetonitrile.

3. The process according to claim 1, wherein the conversion temperature is from 800° to 950° C.

4. The process according to claim 2, wherein the conversion temperature is from 800° to 950° C.

* * * * *